United States Patent [19]

Allard et al.

[11] Patent Number: 5,605,804
[45] Date of Patent: *Feb. 25, 1997

[54] DIAGNOSIS AND MONITORING OF LUNG CANCER PATIENTS BY MEASUREMENT OF NCA 50/90 IN BLOOD

[75] Inventors: William J. Allard, Poughquag, N.Y.; Kwok K. Yeung, Prospect, Conn.

[73] Assignee: Bayer Corporation, Tarrytown, N.Y.

[*] Notice: The term of this patent shall not extend beyond the expiration date of Pat. No. 5,593,847.

[21] Appl. No.: 400,152

[22] Filed: Mar. 7, 1995

Related U.S. Application Data

[63] Continuation of Ser. No. 193,976, Feb. 8, 1994, abandoned, which is a continuation-in-part of Ser. No. 51,111, Apr. 21, 1993, abandoned.

[51] Int. Cl.$^6$ .................... G01N 33/574; G01N 33/48; G01N 33/53; G01N 33/543
[52] U.S. Cl. .................... 435/7.23; 435/7.2; 435/7.94; 436/63; 436/64
[58] Field of Search .................... 435/7.2, 7.23; 436/64; 530/387.7

[56] References Cited

PUBLICATIONS

Radosevich et al, "Immunohistochemical analysis of pulmonary and pleural neoplasms using a monoclonal antibody (47D10) which reacts with nonspecific cross-reacting antigen," vol. 10, pp. 281–288 1989.

*Primary Examiner*—Toni R. Scheiner
*Assistant Examiner*—Yvonne Eyler
*Attorney, Agent, or Firm*—Andrew L. Klawitter

[57] ABSTRACT

A method for aiding in the diagnosis of, and monitoring the progression or course of, lung cancer in a patient by measuring the amount of NCA 50/90 in a blood sample, e.g., serum sample, obtained from the patient. Measurement in a single sample of an amount of NCA 50/90 significantly higher than the mean amount of NCA 50/90 in the normal population is an indication of lung cancer in a symptomatic patient. The course of lung cancer can also be monitored by performing a series of specific immunoassays over time to determine changes in the level of NCA 50/90 in blood samples. Increases in blood NCA 50/90 levels over time are indicative of a deteriorating condition whereas decreasing levels of blood NCA 50/90 over time indicate an improving condition.

15 Claims, 7 Drawing Sheets

DIAGNOSIS AND MONITORING OF LUNG CANCER PATIENTS BY MEASUREMENT OF NCA 50/90 IN BLOOD

CROSS-REFERENCE TO RELATED APPLICATIONS

This is a continuation of application Ser. No. 08/193,976, filed Feb. 8, 1994, now abandoned, which is a continuation-in-part of application Ser. No. 08/051,111, filed Apr. 21, 1993, now abandoned.

BACKGROUND OF THE INVENTION

The present invention relates to the diagnosis of, and monitoring the progression, course, or stage of disease in lung cancer patients. More particularly, the invention relates to such diagnostic and monitoring methods based on measurement of cancer marker blood levels.

A number of substances have been determined to be useful markers in monitoring the course of various cancer types. Some useful markers that have been identified are oncofetal antigens such as carcinoembryonic antigen (CEA) and alpha-fetoprotein, tissue-specific antigens such as prostate-specific antigen (PSA), and mucin antigens such as those conventionally known as CA-125 and CA-19-9. Immunoassays for antigens such as these are typically used as confirmatory tests at the time of diagnosis and subsequently for monitoring patient status. Occasionally, the use of such tests crosses the boundaries of tumor type (for example, the use of CEA tests in colon, breast, and lung cancer, and alpha-fetoprotein in hepatocellular and testicular cancer), but the utility of each test type is foremost for a single tumor type (for example, PSA for prostate cancer and CA-125 for ovarian cancer).

A family of antigenic proteins have been identified which are genetically and immunologically related to CEA (Thompson, J. and W. Zimmerman (1988) Tumor Biol. 9, 63–83; and Barnett, T. and W. Zimmerman (1990) Tumor Biol. 11, 59–63). Among these are the nonspecific cross-reacting antigens (NCAs), the trans-membrane antigens designated biliary glycoprotein (BGP, and sometimes referred to as TM-CEAs), and the family of pregnancy-specific β-glycoproteins (PSGs) (for a description of the accepted nomenclature of these genes and their protein products, reference can be made to: Barnett, T. and W. Zimmerman (1990) Tumor Biol. 11, 59–63). Molecular cloning of the CEA gene family has enabled the identification of 22 members, of which 20 are probably expressed (Frangsmyr, L. et al. (1992) Tumor Biol. 13, 98–99; and Hammerstrom, S. et al Tumor Biol. 13, 57). The results of molecular genetic analysis have given a better understanding of the complex group of glycoproteins in the CEA gene family.

NCA was originally described as a component of normal tissue which cross-reacted with antibodies raised to CEA (Mach, J.-P. and G. Pusztaszeri (1972) Immunochemistry 9, 1031–1034; and von Kleist, S., Chavenel, G. and P. Burtin (1972) Proc. Natl. Acad. Sci. USA 69, 2492–2494). As such, NCA was considered a potential non-tumor derived interferant in assays for CEA. Molecular cloning identified one species of NCA of calculated $M_r$ 37,000 designated by one group as NCA-BT (Barnett, T., Goebel, S. J., Nothdurft, M. A. and J. J. Elting (1988) Genomics 3, 59–66) to denote the breast tissue origin of the cloned cDNA, and by others as NCA (Tawargi, Y. et al. (1988) Biochem. Biophys. Res. Commun. 150, 89–96; and Neumaier, M. et al (1988) J. Biol. Chem. 263, 3203–3207). This single NCA species has since been termed NCA 50/90 (Kolbinger, F., Schwarz, K., Brombacher, F., von Kleist, S., and Grunert, F. (1989) Biochem. Biophys. Res. Commun. 161, 1126–1134) because it was now known to be processed into two mature isoforms of $M_r$ 50,000 and 90,000 which have different degrees of glycosylation. A second and distinct NCA gene was subsequently identified by molecular cloning from leukemic cells that codes for an $M_r$ 95,000 glycoprotein (Kuroki, M. et al (1991) J. Biol. Chem. 266, 11810–11817). This latter NCA has been termed NCA 95.

Early studies also identified a cross-reacting antigen from adult stools and from meconium which, for historical reasons, was termed NCA-2 (Burtin, P., Chavenel, G. and H. Hirsch-Marie (1973) J. Immunol. 111, 1926–1928). Indeed, a recent report suggests that variability in CEA results obtained with different commercial kits may be due to interference with NCA-2 (O. P. Bormer (1991) Clin. Chem. 37, 1736–1739). The designation of this antigen as NCA is, however, a misnomer. It has been identified as a proteolytic fragment of CEA, since the first 30 amino acids of the meconium-derived NCA-2 are identical in sequence with CEA (Siepen, D. et al (1987) Biochem. Biophys. Res. Commun. 174, 212–218). In contrast, cDNAs for NCA 50/90 have been described and code for distinct and different amino acid sequences in this region.

Given the improved understanding of the CEA gene family resulting from molecular cloning analysis, monoclonal antibodies can now be identified which recognize specific family members and do not cross react with closely related molecules. Previous attempts to raise antibodies to NCA have been plagued with the problem of cross reactivity with CEA family members. This may explain why NCA has been considered a poor serum marker for cancer diagnosis and monitoring (Shively, J. E., Spayth, V., Chang, F.-F., Metter, G. E., Klein, L., Present, C. A., and C. W. Todd (1982) Cancer Res. 42, 2502–2513; and Burtin, P., Chavenel, G., Hendrick, J. C. and N. Frenoy (1986) J. Immunol. 137, 839–845). It has been further speculated that NCA-specific monoclonal antibodies such as are now widely accepted for CEA and other antigens would be very difficult to develop (Burtin, P. et al., supra).

In addition, it is now clear that members of the CEA gene family are differentially expressed by various tumor types. For example, it is well known that CEA is expressed in most if not all colorectal carcinomas, while expression is limited to a minority of breast carcinomas. Prior to the generation of specific monoclonal antibodies, attempts to quantitate NCA levels in the serum of cancer patients were confounded by the presence of other CEA gene family members that cross reacted with the antibodies being used. However, because of the successful production of monoclonal antibodies specific to NCA 50/90, it is now possible to determine the incidence of elevated NCA 50/90 protein in different cancer types.

Although there have been reports of monoclonal antibodies specific for NCA 50/90 (Chavenel, G., Frenoy, N., Escribano, M. J. and P. Burtin (1983) Oncodev. Biol. and Med. 4, 209–217; and Yeung, M., M.-W. Hammerstrom, M. L., Baranov, V. and S. Hammerstrom (1992) Tumor Biol. 9, 119), there have been no reports of a monoclonal antibody which binds to NCA 50/90 but does not recognize any other CEA family members including CEA, NCA 95, NCA 2, BGP and PSG. Similarly, several reports have suggested that NCA may be elevated in the serum of cancer patients with solid tumors (von Kleist, S., Troupel, S., King, M. and P. Burtin (1977) Br. J. Cancer 35, 875–880; and Wahren, B., Gahrton, G., Ruden, U. and S. Hammerstrom (1982) Int. J.

Cancer 29, 133–137; and Harlozinska, A., Rachel, F., Gawlikowski, W., Richter, R. and J. Kolodziej (1991) Eur. J. Surg. Oncol. 17, 59–64; and Reck, W., Daniel, S., Nagel, G., Hirn, M., von Kleist, S., and F. Grunert (1992) Tumor Biol. 13, 110–111), but these measurements used antibodies that have not been shown to recognize NCA 50/90 to the exclusion of other CEA-related molecules. In addition, there have been no reports of a correlation between blood NCA levels and the clinical status of patients with solid tumors.

Results of several studies have shown that NCA is elevated in the serum of patients with leukemia, particularly chronic myelocytic leukemia (Frenoy, F. and P. Burtin (1980) Clin. Chim. Acta 103, 23–31; Wahren, B., Gahrton, G. and S. Hammarstrom (1980) Cancer Res. 40, 2039–2044; Wahren, B., Gahrton, G. and S. Hammarstrom (1980) Cancer Res. 40, 2039–2044; Wahren, B., Gahrton, G., Ruden, U. and S. Hammarstrom (1982) Int. J. Cancer 29, 133–137; Frenoy, N., Ben-Bunant, M., Burreul, C., Child, J. A., Gendron, M. C., Missett, J. L., Razafimahaleo, E. and P. Burtin (1982) Br. J. Cancer 46, 765–772). These data show that NCA may be elevated in the early stages of leukemia, but that serum NCA levels decrease during blast crisis. It is not clear from these studies if changes in NCA levels reflect changes in the clinical status of the patients since, in one study, changes in the serum concentration of NCA were reflected by changes in total white cell counts and polymorphonuclear cell counts (Wahren, B. Gahrton, G., Ruden, U. and S. Hammarstrom (1982) Int. J. Cancer 29, 133–137), whereas in other studies, these same parameters either did not correlate or correlated only poorly (Frenoy, F. and P. Burtin (1980) Clin. Chim. Acta 103, 23–31; Frenoy, N., Ben-Bunant, M., Burruel, C., Child, J. A., Gendron, M. C., Missette, J. L., Razafimahaleo, E. and P. Burtin (1982) Br. J. Cancer 46, 765–772). In any event, these studies are difficult to interpret since the methods used to measure NCA in serum used polyclonal antibodies which were not well characterized with respect to their reactivity with various members of the CEA family of molecules.

Previous attempts to quantitate the level of NCA 50/90 in the serum have been hampered by the lack of a suitable standard. Measurements of NCA in blood have shown mean values in serum from normal individuals of from 30 ng/ml (Harlozinska, A., et al. supra) to 130 ng/ml (von Kleist, S., Troupel, S., King, M. and P. Burtin (1977) Br. J. Cancer 35, 875–880). This is due to the use of biochemically purified NCA as a standard to calibrate immunoassay measurements of NCA in blood and blood fluids. Just as the monoclonal antibodies have not been demonstrated to specifically recognize NCA 50/90, neither has the purity of the NCA standard preparations been determined.

U.S. patent application Ser. No. 815,934, filed Dec. 30, 1991, and entitled "Monitoring of NCA-BT in Blood Samples of Breast Cancer Patients", reports the finding that changes in the blood level of NCA 50/90 (therein designated as NCA-BT) in breast cancer patients provides a means for monitoring the progression of the disease. In particular, it was found that increases in blood NCA 50/90 levels measured by performing a series of specific immunoassays over time indicated a deteriorating condition in a significant number of patients, while decreases in blood NCA 50/90 levels indicated an improving condition in such patients.

SUMMARY OF THE INVENTION

It has now been found that NCA 50/90 can be significantly elevated in the blood of patients with lung cancer. Accordingly, the present invention provides a method for aiding in the diagnosis of lung cancer in a patient who presents with symptoms of lung cancer (i.e., a symptomatic patient), comprising the steps of determining the amount of NCA 50/90 in a blood sample obtained from said patient and comparing such measured amount of NCA 50/90 to the mean amount of NCA 50/90 in the normal population, whereby the presence of a significantly increased higher amount of NCA 50/90 in the patient's blood is an indication of lung cancer in the patient. With this and other information suggestive of lung cancer, the physician is assisted in making a diagnosis.

The present invention also provides a method for monitoring the course or progression of lung cancer in a patient who has been diagnosed with lung cancer. A series of specific immunoassays are performed over time to determine changes in the level of NCA 50/90 in blood samples obtained from such patient, whereby changes in the NCA 50/90 blood level correlate with changes in disease status. More particularly, increases in blood NCA 50/90 levels will generally indicate a deteriorating condition while decreases in blood NCA 50/90 levels indicate an improving condition. Where the diagnosed patient has been treated for lung cancer, e.g., radiation, chemotherapy, surgery, or the like, increases in blood NCA 50/90 levels indicate recurrence of disease.

DESCRIPTION OF THE PREFERRED EMBODIMENTS

Figure 1:
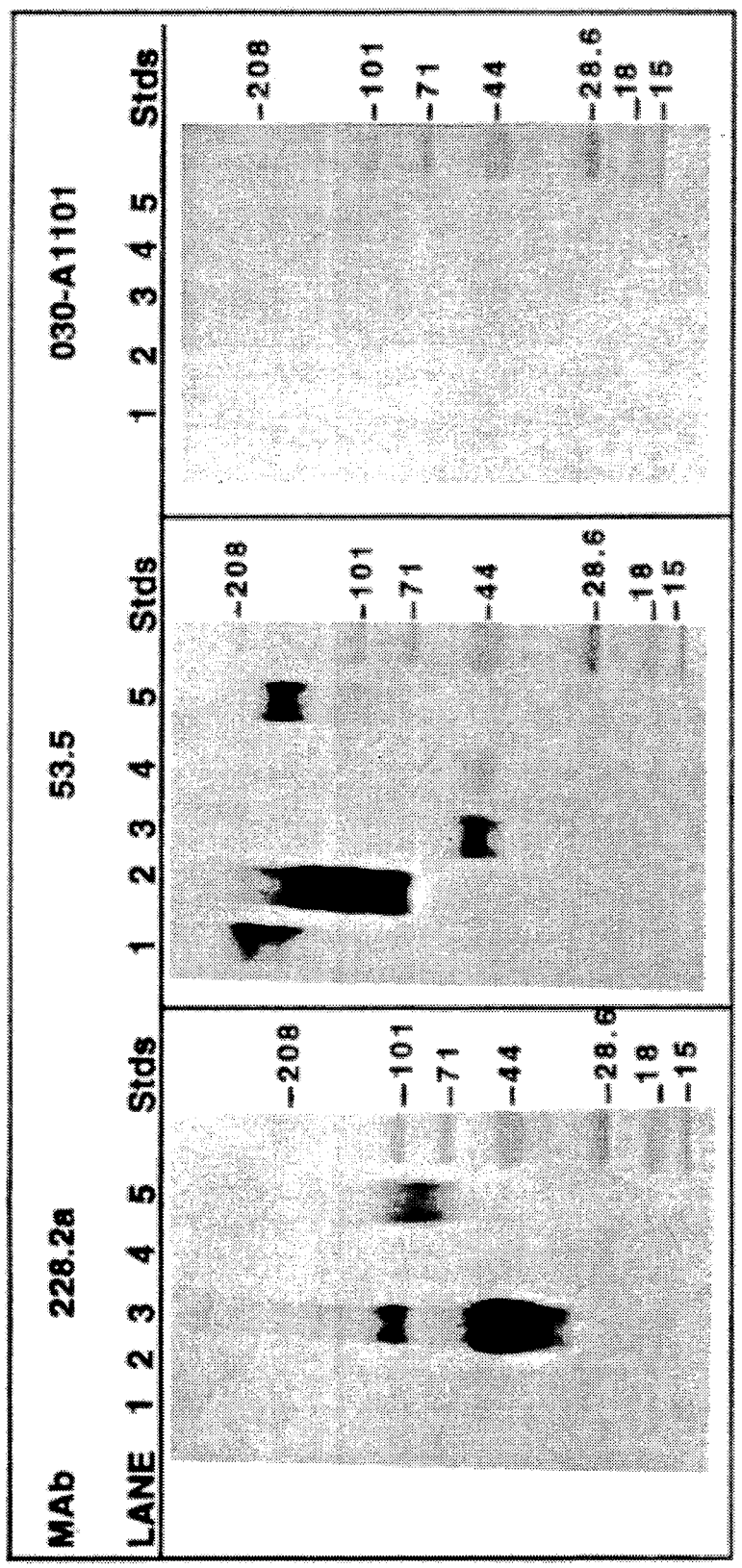
FIG. 1 is a reproduction of a Western blot showing that the 228.2 monoclonal antibody (more specifically described hereinbelow, and particularly in the Examples) binds to NCA 50/90, but does not recognize NCA 95, CEA, BGPs, or NCA 2. For each of the three blots presented, the indicated monoclonal antibodies were blotted against CEA family members as follows: lane 1, CEA; lane 2, BGP; Lane 3, NCA 50/90; lane 4, NCA 95; lane 5, NCA 2. The control blots in the figure also show that the preparation of NCA 50/90 used as a standard in the NCA 50/90 ELISA assay contains only NCA 50/90.

Essentially any method may be employed in the measurement of blood (e.g., serum or plasma) NCA 50/90 levels. Typically, such measurement will be performed by sandwich immunoassay using two antibody reagents, one of which recognizes NCA 50/90 to the exclusion of other related members of the CEA family (e.g., NCA 95, CEA, BGP, PSG, and NCA 2), while the other is capable of binding specifically or nonspecifically with NCA 50/90. Assay format and methods for the preparation of the required antibody reagents can be selected by the skilled worker in the field. Suitable antibody reagents can be labeled, e.g., enzyme-labeled, or immobilized, e.g., coated onto a microtiter plate, bound to plastic or magnetic beads or particles, and can be comprised of whole immunoglobulins, e.g., IgG or IgM, or fragments, e.g., Fab, Fab', and F(ab')$_2$ fragments, or aggregates thereof.

Preferably, the NCA 50/90 specific antibody reagent is prepared by immunization of a host animal with a suitable immunogen such as an NCA 50/90-containing immunogen mixture, e.g., a purified extract of spleen or tumor cells; NCA 50/90-expressing transfectant cell lines (see European Patent Publication 346,702); an immunogen conjugate comprising a synthetically prepared peptide coupled to a conventional immunogenic carrier molecule, where the peptide has an amino acid sequence encompassing an epitope of NCA 50/90; and the like as will be understood in the art.

Antibody reagents comprising monoclonal antibodies will be generally preferred. Particularly preferred NCA 50/90 specific monoclonal antibodies are those which bind to substantially the same epitope as that produced by the hybridoma that was deposited on Nov. 18, 1992, with the American Type Culture Collection, 12301 Parklawn Drive, Rockville, Md. 20852 and which has been given deposit accession number ATCC HB 11204. It will be understood that a number of standard methods can be used in order to determine whether a particular monoclonal antibody binds to substantially the same epitope as the above-mentioned antibody whose hybridomas have been deposited with the ATCC. A particularly useful method is competitive binding, wherein the ability of the antibody of interest to bind to NCA 50/90 in the presence of the reference antibody is measured. Substantial inability of both antibodies to bind simultaneously indicates that substantially the same epitope is involved.

It will be understood that, similar to other types of accepted disease diagnostic and monitoring methods, the present method will not be useful on every patient diagnosed with lung cancer. Rather, the physician will use NCA 50/90 blood values in combination with other diagnostic values and clinical observations to diagnose the onset of lung cancer, and further to develop a course of treatment and therapy for each individual patient. It is also contemplated that monitoring blood levels of NCA 50/90 will provide a means for monitoring the progress of a course of therapy for an individual patient.

The present invention will now be illustrated, but is not intended to be limited by, the following examples.

EXAMPLES

MAb 228.2—BALB/C mice were immunized with 50 μg of an emulsion of NCA purified from human spleen (von Kleist, S. and P. Burtin (1969) Cancer Res. 29:1961–1964), and Freund's complete adjuvant. Spleens from hyperimmune animals were removed from euthanized animals and the splenocytes were fused with AG8 mouse myeloma cells (ATCC CRL 1580). The resulting hybridomas were screened for anti-NCA antibody production by sandwich ELISA. Positive clones were subsequently screened for anti-CEA and anti-TM-CEA(BGP) activity (see Barnett, T. and W. Zimmerman supra; and see Barnett, T. R., Kretschmer, A., Austen, D. A., Goebel, S. J., Hart, J. T., Elting, J. J., and M. E. Kamarck (1989) J. Cell Biol. 108:267–276) by sandwich ELISA assay. Those clones specific for NCA 50/90 were recloned and rechecked for cross reactivity with CEA and TM-CEA(BGP) by ELISA and again by FACS analysis using recombinant mouse cell lines expressing CEA, NCA 50/90 or TM-CEA on their plasma membranes (see European Patent Publication No. 346,702). The result of this screening process was identification of MAb 228.2 (deposited with the ATCC, supra) which is specific for NCA 50/90 with no detectable reactivity with CEA, NCA-CML or TM-CEA by ELISA.

Control MAbs—The 53.5 MAb was derived by procedures similar to those described above for the 228.2 MAb except that purified CEA from liver metastases (Catalog #CO224, Scripps Laboratories, San Diego, Calif.) was used as the immunogen and primary screening was by ELISA using purified CEA as the antigen. This antibody reacts on Western blots with CEA, BGP, NCA 50/90, NCA 95, and NCA 2, and is used as a positive control.

The Mab designated 030-A1101 is an IgG1 which binds to alpha fetoprotein (AFP), and was obtained from BiosPacific (Emeryville, Calif.). It was used in these studies as a negative control.

Biotinylation of Goat Antibody to CEA—An affinity purified polyclonal goat antiserum raised to CEA was purchased from BiosPacific, Emeryville, Calif., USA (Lot No. 015-B4302) and placed into 1.3 ml of 0.1M NaHCO$_3$, pH 8.5 at a concentration of 1.0 mg/ml. To this was added 18.5 μl of a 10 mg/ml solution of NHS-LC-biotin (Pierce, Rockford, Ill., USA, Catalog No. 21335) in deionized water to give a 50/1 molar excess of biotin to antibody. After incubation at 0° C. for 4 hours the biotinylated antibody was passed over a buffer-exchange column using 10 mM phosphate, pH 7.4/150 mM NaCl and stored at 4° C. with 0.1% thimerosal as preservative.

NCA Calibrator—A CDNA corresponding to NCA 50/90 was derived from the breast tumor cell line BT-20 as described previously (Barnett, T., Goebel, S. J., Nothdurft, M. A. and J. J. Elting (1988) Genomics 3, 59–66). The coding region for the NCA 50/90 gene was modified by the elimination of the C-terminal hydrophobic region which signals replacement by a phosphoinositol glycan linkage, and the addition of a stretch of six histidine residues, also at the carboxyl terminus of the molecule (Drake, L. and Barnett, T. (1992) Biotechniques 12, 645–649). This construct was cloned into pVL1393 by PCR and expressed using recombinant baculovirus to infect Spodoptera frugiperda (Sf9) cells. NCA 50/90 was affinity purified from Sf9 supernatant fluids using a zinc-imidoacetate-Sepharose® column as described (Drake and Barnett, supra). The concentration of NCA was determined by the BCA protein assay (Pierce, Cat. No. 23225G). For use as a calibrator in the NCA 50/90 ELISA, purified recombinant NCA 50/90 was diluted in TBST/5% BSA as described below.

NCA 50/90-Specific Immunoassay—A sandwich ELISA was configured using the 228.2 monoclonal antibody as the solid phase capture antibody, and the biotinylated polyclonal anti-CEA as the reporter antibody. 96-well ELISA plates (Immulon 4, Dynatech Laboratories, Chantilly, Va., USA) were coated with 100 μl of 228.2 antibody at 5 μg/ml in 0.1M NaHCO$_3$, pH 9.5 and incubated overnight at 4° C. Wells were emptied and unreacted sites on the plates were quenched by the addition of 200 μl of 20 mM Tris, pH 7.5/150 mM NaCl/0.05% Tween 20 (TBST) with 5% bovine albumin (BSA, fraction V, Sigma Chemical Company, St. Louis, Mo., USA, Catalog No. A-7030) followed by a 1 hour incubation at 37° C. Wells were washed 6 times with TBST, and 25 µl of either NCA 50/90 calibrators diluted in TBST/5% BSA or 25 µl of patient sample was added. An equal volume of 50 mM HEPES, pH 7.0/500 mM NaCl/200 µg/ml mouse IgG/5% BSA/50 µg/ml gentamycin/0.1% (w/v) NaN$_3$ (sample diluent) was added to each well and the plates were incubated for 2 hours at 37° C. After washing 6 times, a 100 µl volume of a 0.3 µg/ml solution of goat anti-CEA-biotin in 50 mM HEPES, pH 7.0/150 mM NaCl/1 mM MgCl$_2$.H$_2$O/0.1 Mm ZnCl$_2$/5% BSA/50µg/ml gentamycin/0.1% NaN$_3$ (conjugate diluent) was added to all wells and incubated for 1 hour at 37° C. The wells were washed a further 6 times, and 100 µl of streptavidin conjugated to alkaline phosphatase (Pierce, Catalog No. 21324G) diluted 1/5000 in conjugate diluent was added. After a 1 hour incubation at 37° C., the plates were washed 12 times with TBST and incubated with 100 µl of p-nitrophenyl phosphate in DEA substrate buffer (Pierce, Catalog No. 34064) for 30 minutes. The reaction was stopped with 100 µl 1N NaOH and absorbance at 405 nm minus absorbance at 490 nm determined using a microplate reader (Thermo-Max, Molecular Devices Corp., Menlo Park, Calif., USA). The amount of NCA 50/90 was determined for each test sample by comparison with the calibrator standard curve.

Patient Samples—Serum was prepared from blood drawn from normal healthy volunteers by Hudson Valley Blood Services of Valhalla, N.Y., USA. Samples from patients with inactive or active lung cancer were obtained from Dianon Systems of Stratford, Conn., USA. Longitudinal serum samples drawn from individual patients during the period of treatment were obtained from M. D. Anderson Cancer Center in Houston, Tex., USA. Patient disease status was determined from information supplied by attending physicians as well as results of testing for the tumor markers CEA, lipid associated sialic acid (LASA), and neuron specific enolase (NSE).

Results

The antigenic specificity of the 228.2 monoclonal antibody was determined first by Western blotting and results are shown in FIG. 1. The 228.2 MAb reacts specifically with NCA 50/90 and not with other proteins related to CEA. The reactivity of the 228.2 Mab with the high molecular weight band of $M_r$ 110,000 probably represents the formation of SDS-stable protein dimers. The reactivity of the 228.2 MAb with the NCA 2 preparation is with an $M_r$ 90,000 protein which does not comigrate with the $M_r$ 160,000 NCA 2 protein, and is likely to represent a low level of contamination of the NCA 2 preparation with the $M_r$ 90,000 form of NCA 50/90. The reactivity of the positive control MAb 53.5 with each of the antigen preparations demonstrates the presence of the relevant glycoproteins in each preparation. In addition, the 53.5 MAb reacted only with a protein of $M_r$ 50,000 in the NCA 50/90 preparation, which demonstrates the antigenic purity of the NCA 50/90 preparation. The MAb 030-A1101 binds to alpha fetoprotein and was used as negative control.

Figure 2:
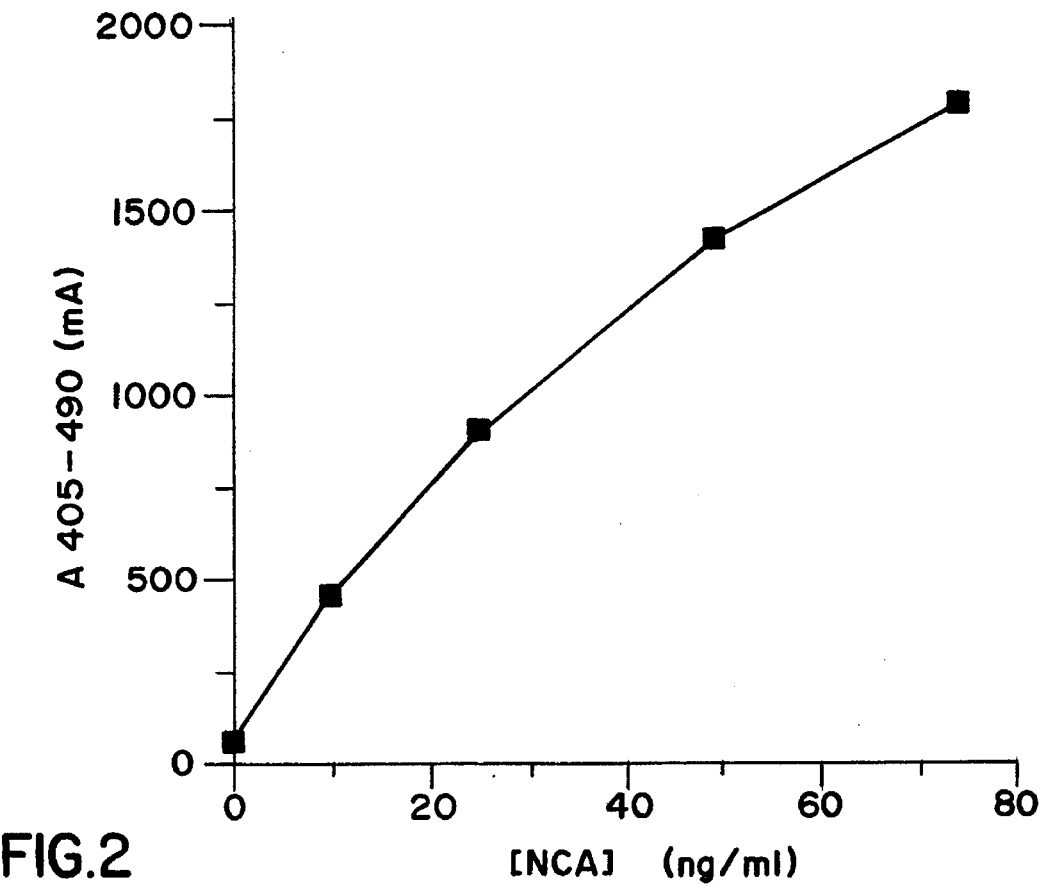
FIG. 2 is a graph showing the standard curve obtained in the NCA 50/90 ELISA assay.
Figure 3:
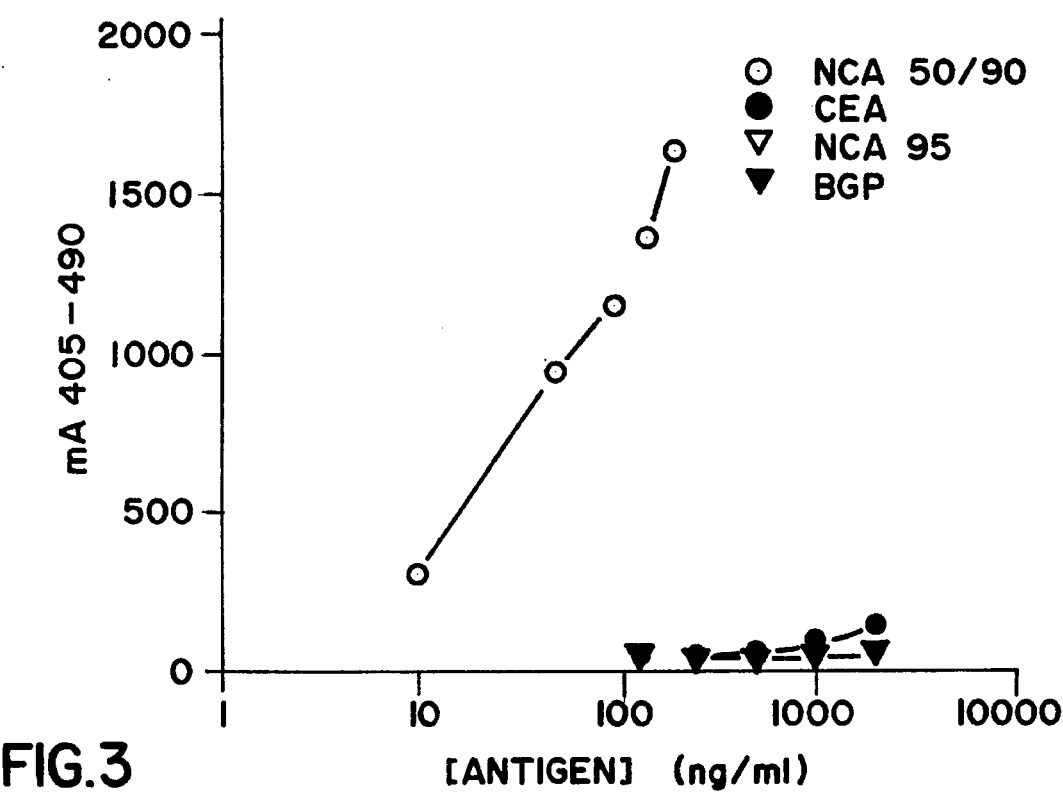
FIG. 3 is a graph showing that the NCA 50/90 ELISA assay exhibits no significant cross-reactivity with NCA 95, CEA, or BGP.
Figure 4:
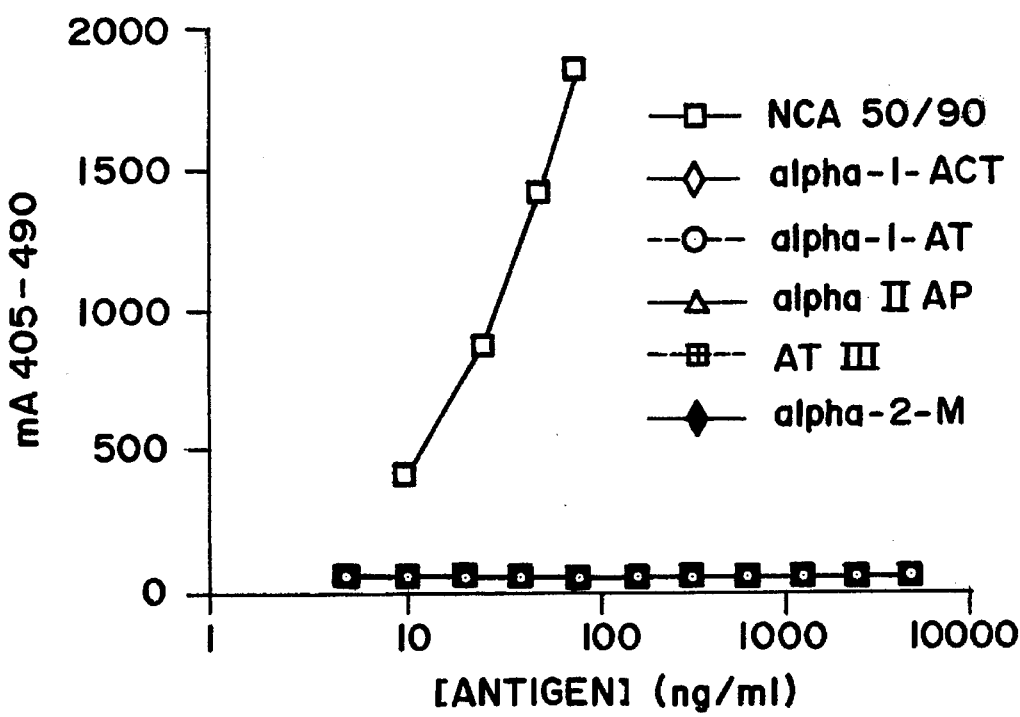
FIG. 4 is a graph showing that the NCA 50/90 ELISA assay exhibits no significant cross-reactivity with α-1-antichymotrypsin, α-1-antitrypsin, α-2-macroglobulin, α-2-anti-plasmin, or antithrombin III.

The standard curve presented in FIG. 2 demonstrates a non-linear increase in absorbance as a function of NCA 50/90 concentration. A nonlinear spline curve fit program was used to convert raw patient data to NCA 50/90 concentrations. The data in FIGS. 3 and 4 demonstrate that the NCA 50/90 ELISA shows no significant reactivity with CEA, NCA 95, BGPs, α-1-antichymotrypsin, α-1-antitrypsin, α-2-macroglobulin, α-2-antiplasmin and antithrombin III. The potential for cross reactivity with serine proteinase inhibitors stems from observations that biochemically purified CEA and NCA may associate with molecules with amino acid homology to α-1-antichymotrypsin and α-1-antitrypsin (Orjaseter, H. (1976) Acta Path. Microbiol. Scand. 84, 235–244; and Grunert, F., Abuharfeil, N., Luckenbach, G. A. and S. von Kleist (1984) Tumor Biol. 5, 221–232). Since the MAb 228.2 was raised to biochemically purified NCA 50/90 from spleen, there is some potential for cross reactivity with contaminating proteins.

Figure 5:
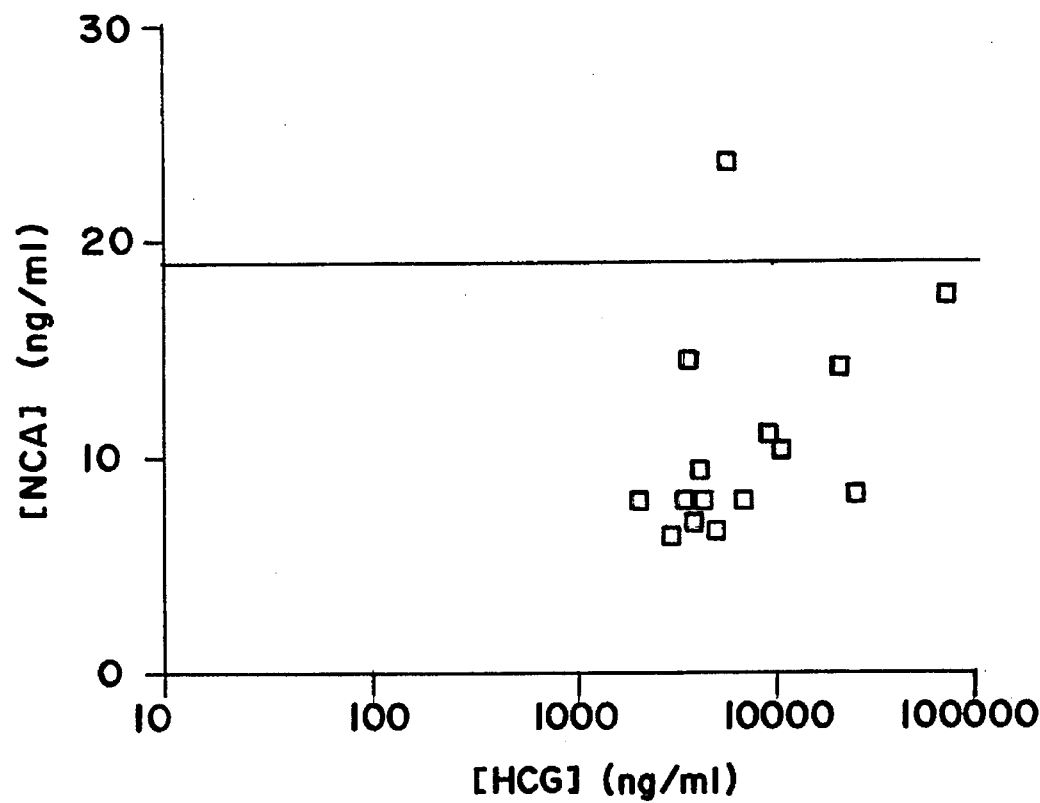
FIG. 5 is a graph showing that the NCA 50/90 ELISA assay exhibits no significant reactivity with serum from pregnant women, demonstrating no significant cross-reactivity with PSG.
Figure 6:
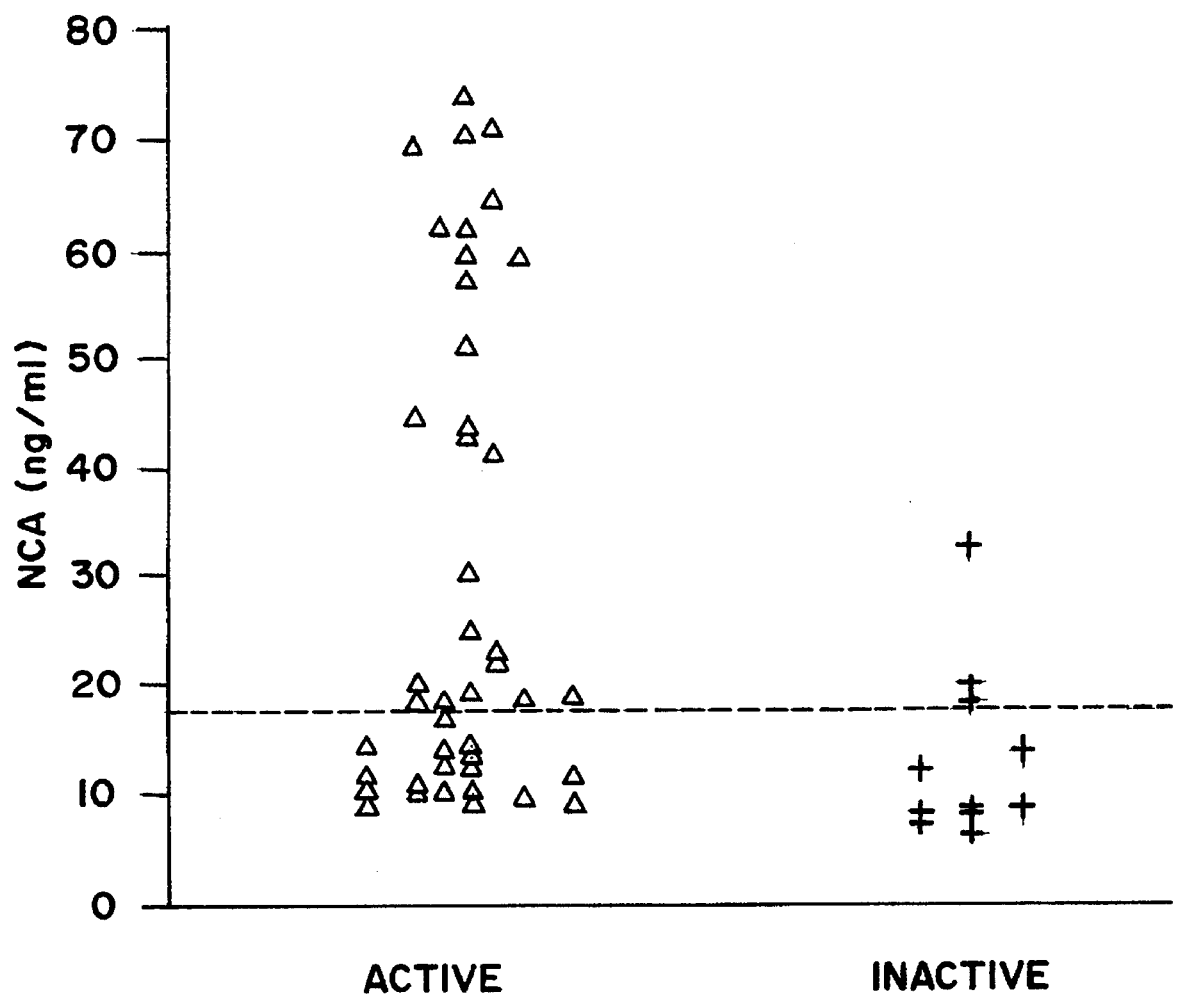
FIG. 6 is a graph showing that the level of NCA 50/90 is elevated in the serum of patients with lung cancer.
Figure 7:
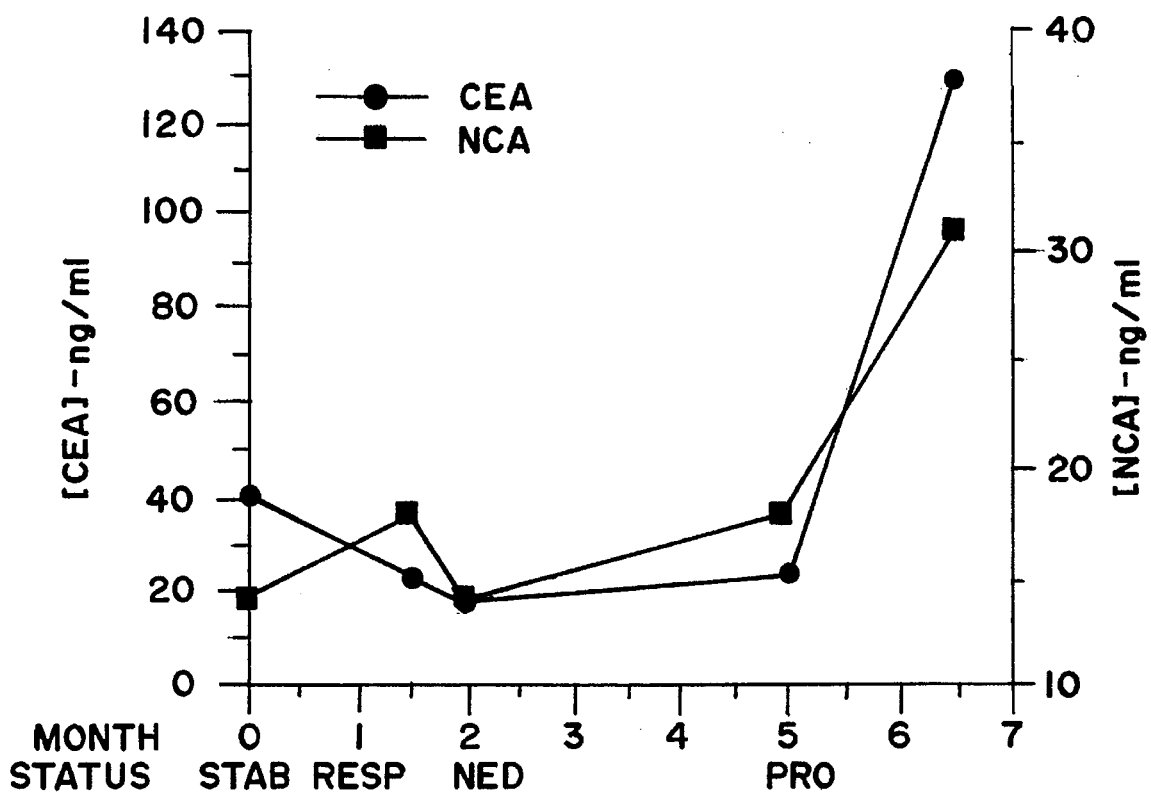
FIGS. 7–11 are a series of graphs showing the course of NCA 50/90 levels over time in serum samples of individual patients with lung cancer.
Figure 8:
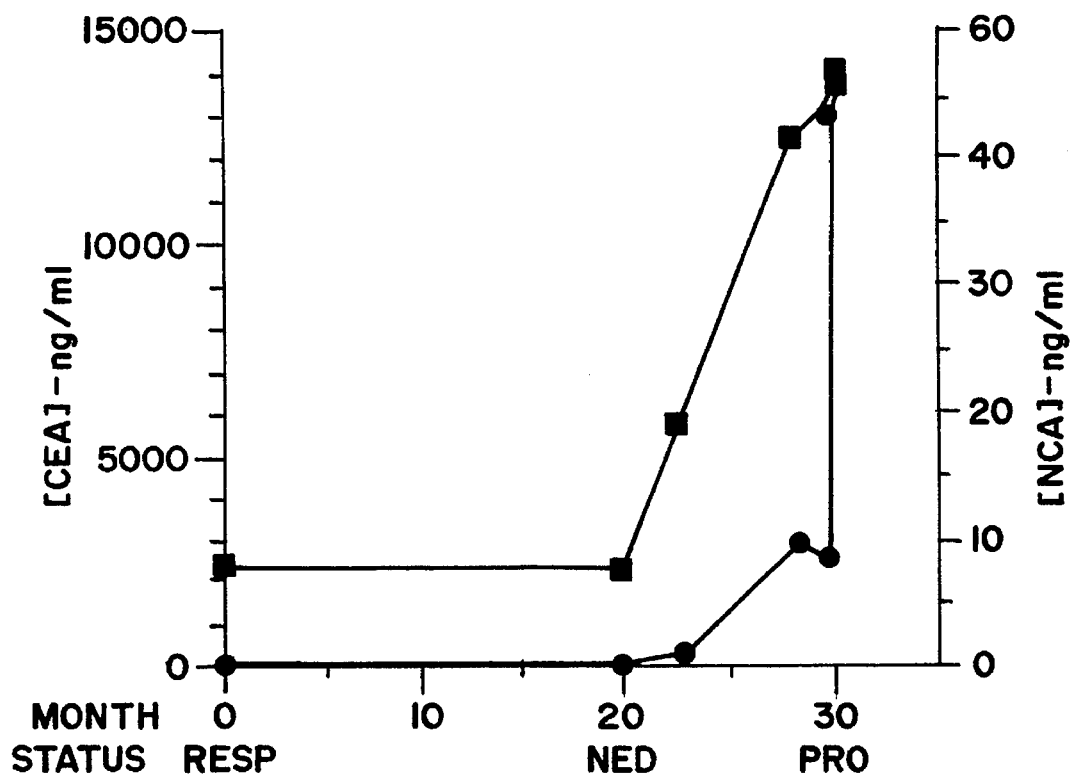
Figure 9:
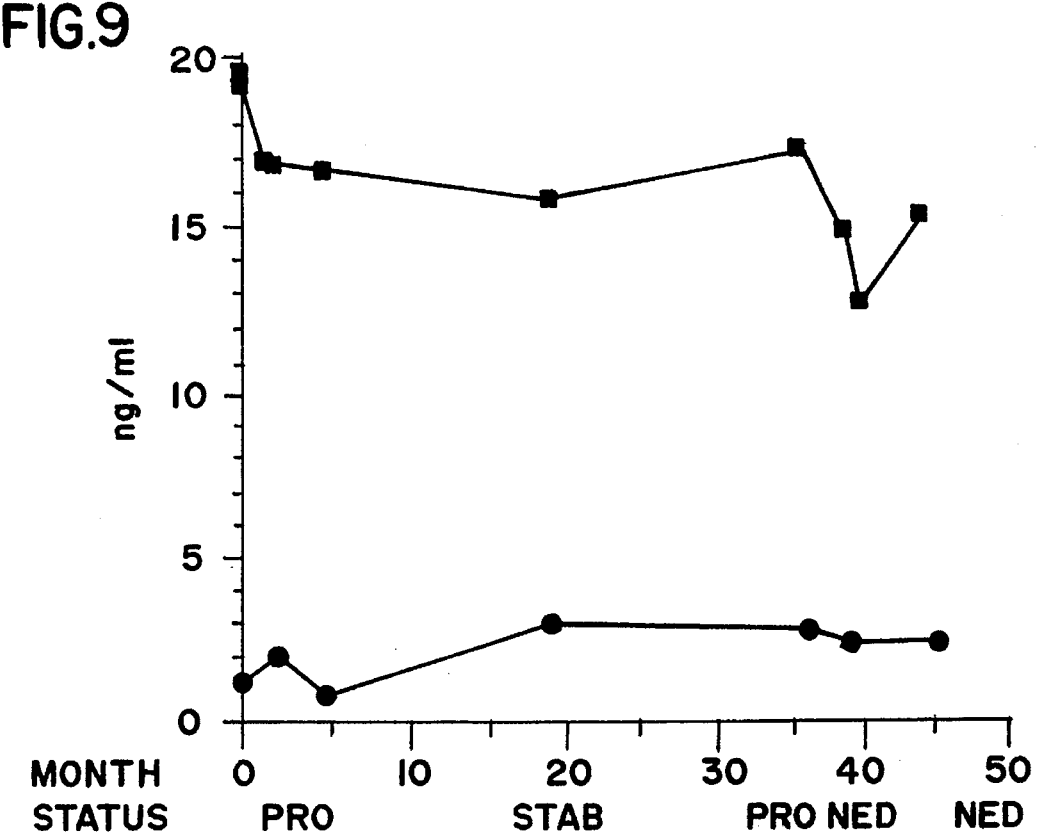
Figure 10:
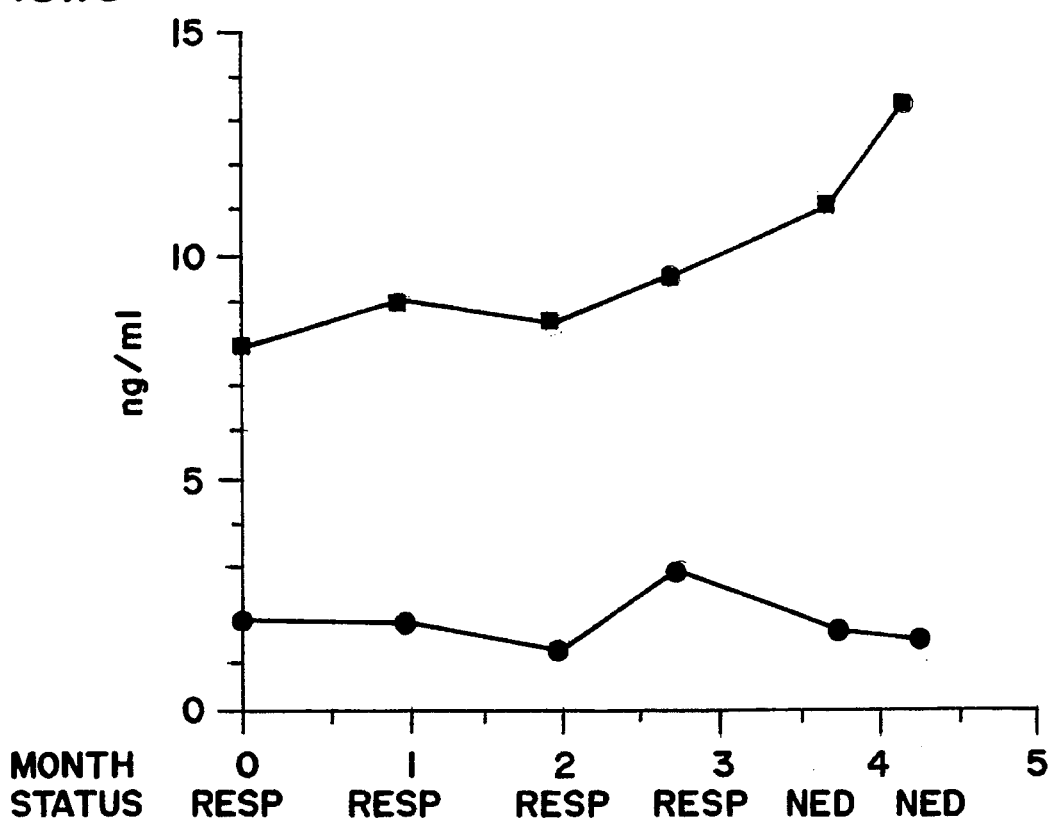
Figure 11:
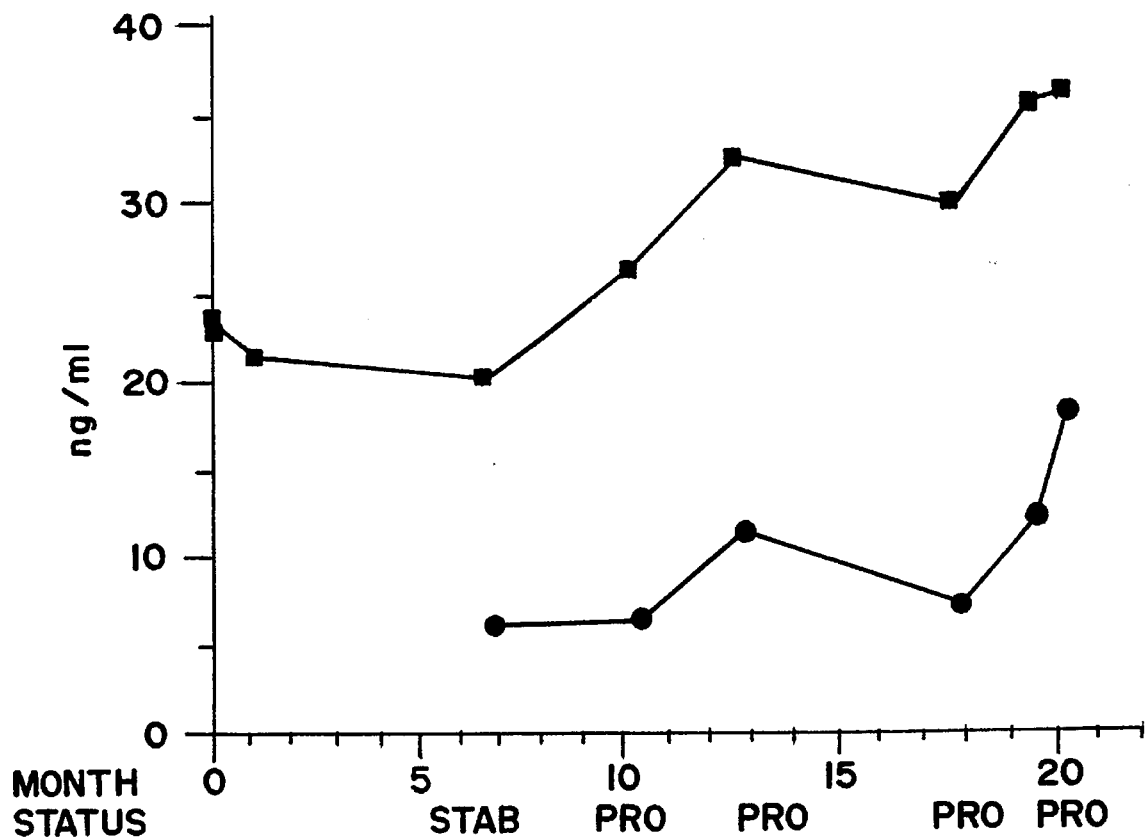

An additional member of the CEA gene family is pregnancy specific β-glycoprotein (PSG) which is elevated in the serum of pregnant women. Reactivity to this protein was tested by examining sera from 15 pregnant women with HCG values ranging from 2200 to 79,000 (normal cutoff for HCG=10). As can be seen in FIG. 5, only one patient showed an NCA value above the cutoff value of 18 ng/ml, which demonstrates that the NCA 50/90 ELISA does not detect PSG.

To establish a cutoff value for normal blood levels of NCA 50/90, the level of NCA 50/90 in serum was measured from 92 normal healthy volunteers. A 95% cutoff value was determined to be 18 ng/ml. NCA 50/90 values in plasma from 10 lung cancer patients undergoing treatment who were clinically free of cancer was then measured, and it was found that 8/10 of the values were below the cutoff value. In contrast, 70% of the samples from patients with active lung cancer were above the cutoff value, which demonstrates that NCA 50/90 is elevated above normal levels in the blood of some patients with lung cancer. Similar results were found with untreated patients with lung cancer where 7/16 samples had levels of NCA 50/90 which exceeded the cutoff limit. The high incidence of elevated values of NCA 50/90 in the blood of lung cancer patients shows that the present method is useful to detect cancer in patients.

The serum level of NCA 50/90 was found to correlate with the status of disease in six patients diagnosed with and under treatment for lung cancer. Results obtained with samples from five of these patients are presented in FIGS. 7–11.

The terms used in FIGS. 7–12 to denote patient status are defined as follows:

NED—No clinical evidence of disease as determined by the attending physician and verified by normal blood levels of at least two biomarkers.

PRO—Clinical evidence of progressive disease as determined by the attending physician and verified by elevated blood levels of at least one cancer biomarker.

STAB—Clinically stable cancer with no evidence of disease progression since the last examination.

RESP—Responding to treatment with at least a 50% decrease in the tumor mass since diagnosis.

Patients LS1 and LS6 had inactive cancer in the early stages of the study, but developed recurrent disease at later time points. Both CEA and NCA showed elevated values when the clinical condition worsened from No Evidence of Disease (NED) to Progressive Disease (PRO), as determined by the attending physician. It should be noted, however, that the NCA values for Patient LS6 were elevated prior to the clinical finding of disease recurrence and prior to increases in the level of CEA. Results with Patient LS4 remained below cutoff for both NCA and CEA throughout the course of the study which is in agreement with the clinical condition of this patient. Patient LS2 remained free of clinically detectable disease throughout the course of the study, and the NCA levels also remained below cutoff. The values of the later samples showed an increasing trend, however, and it would be of interest to know if this patient suffered recurrent disease following collection of these samples. Unfortunately, such information was not available. The combined results with all six patients demonstrate that NCA 50/90 values correctly reflected disease status in 89% of the longitudinal samples. Taken together, these results demonstrate that NCA 50/90 can be used to monitor disease status in lung cancer patients under treatment.

The present invention has been particularly described and exemplified above. Clearly, many other variations and modifications of the invention can be made without departing from the spirit and scope hereof.

What is claimed is:

1. A method for monitoring the course of disease in a patient diagnosed with lung cancer, comprising the performance of a series of specific immunoassays over time to determine changes in the level of NCA 50/90 in blood samples obtained from such patient, whereby changes in the NCA 50/90 blood level correlate with changes in disease status.

2. The method of claim 1 wherein the immunoassays performed are sandwich immunoassays in which at least one of the antibody reagents is specific for NCA 50/90 with no substantial reactivity for CEA, NCA 95, or BGP.

3. The method of claim 2 wherein said NCA 50/90 specific antibody reagent is a monoclonal antibody reagent.

4. The method of claim 1 wherein said NCA 50/90 specific antibody reagent is the monoclonal antibody produced by the hybridoma deposited with the American Type Culture Collection and identified as ATCC HB11204, or a monoclonal antibody which binds to the same epitope as the aforesaid monoclonal antibody produced by hybridoma ATCC11204.

5. The method of claim 1 wherein said blood samples are serum or plasma samples.

6. A method for monitoring the course of disease in a patient diagnosed with lung cancer, comprising the performance of a series of specific immunoassays over time to determine changes in the level of NCA 50/90 in blood samples obtained from such patient, whereby increases in blood NCA 50/90 levels indicate a deteriorating condition while decreases in blood NCA 50/90 levels indicate an improving condition.

7. The method of claim 6 wherein the immunoassays performed are sandwich immunoassays in which at least one of the antibody reagents is specific for NCA 50/90 with no substantial reactivity for CEA, NCA 95, or BGP.

8. The method of claim 7 wherein said NCA 50/90 specific antibody reagent is a monoclonal antibody reagent.

9. The method of claim 6 wherein said NCA 50/90 specific antibody reagent is the monoclonal antibody produced by the hybridoma deposited with the American Type Culture Collection and identified as ATCC HB11204, or a monoclonal antibody which binds to the same epitope as the aforesaid monoclonal antibody produced by hybridoma ATCC11204.

10. The method of claim 6 wherein said blood samples are serum or plasma samples.

11. A method for monitoring the course of disease in a patient who has been treated for lung cancer, comprising the performance of a series of specific immunoassays over time to determine changes in the level of NCA 50/90 in blood samples obtained from such patient, whereby increases in blood NCA 50/90 levels indicate recurrence of disease.

12. The method of claim 11 wherein the immunoassays performed are sandwich immunoassays in which at least one of the antibody reagents is specific for NCA 50/90 with no substantial reactivity for CEA, NCA 95, or BGP.

13. The method of claim 12 wherein said NCA 50/90 specific antibody reagent is a monoclonal antibody reagent.

14. The method of claim 11 wherein said NCA 50/90 specific antibody reagent is the monoclonal antibody produced by the hybridoma deposited with the American Type Culture Collection and identified as ATCC HB11204, or a monoclonal antibody which binds to the same epitope as the aforesaid monoclonal antibody produced by hybridoma ATCC11204.

15. The method of claim 11 wherein said blood samples are serum or plasma samples.

* * * * *